United States Patent
Collins et al.

(10) Patent No.: US 8,338,088 B2
(45) Date of Patent: Dec. 25, 2012

(54) METHODS RELATED TO CELL SURFACE GLYCOSYLATION

(75) Inventors: Brian Edward Collins, Arlington, MA (US); Carlos J. Bosques, Arlington, MA (US); Xiangping Zhu, North Grafton, MA (US); Dorota A. Bulik, Malden, MA (US); Lakshmanan Thiruneelakantapillai, Boston, MA (US); Ian Christopher Parsons, Belmont, MA (US); Zachary Shriver, Cambridge, MA (US); Rajeev Chillakuru, Cambridge, MA (US); Ganesh Venkataraman, Bedford, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 315 days.

(21) Appl. No.: 12/595,902

(22) PCT Filed: Apr. 15, 2008

(86) PCT No.: PCT/US2008/060355
§ 371 (c)(1),
(2), (4) Date: Feb. 25, 2010

(87) PCT Pub. No.: WO2008/128228
PCT Pub. Date: Oct. 23, 2008

(65) Prior Publication Data
US 2010/0196940 A1 Aug. 5, 2010

Related U.S. Application Data

(60) Provisional application No. 60/923,655, filed on Apr. 16, 2007.

(51) Int. Cl.
*C12Q 1/00* (2006.01)
(52) U.S. Cl. ............................................. 435/4
(58) Field of Classification Search .................. None
See application file for complete search history.

(56) References Cited

U.S. PATENT DOCUMENTS

| 5,122,469 A | 6/1992 | Mather et al. |
| 5,633,162 A | 5/1997 | Keen et al. |
| 2007/0148165 A1 | 6/2007 | Shitara et al. |

FOREIGN PATENT DOCUMENTS

| WO | WO98/26277 | 6/1998 |
| WO | WO-2004/019040 A1 | 3/2004 |
| WO | WO-2006/029130 A2 | 3/2006 |
| WO | WO 2007/012695 A2 * | 2/2007 |
| WO | WO-2007/012695 A2 | 2/2007 |
| WO | WO-2008/130926 A2 | 10/2008 |
| WO | WO-2008/131041 A1 | 10/2008 |

OTHER PUBLICATIONS

Suzuki et al (International Journal of Oncology, 2006, 28: 155-160).*
Anumula. (2006) "Advances in fluorescence derivatization methods for high-performance liquid chromatographic analysis of glycoprotein carbohydrates," Analytical Biochemistry. 350(1):1-23.
Chintalacharuvu et al. (1997) "The glycosylation of IgA produced by murine B cells is altered by Th2 cytokines," J. of Immunology. 159(5):2327-2333.
Choi et al. (2003) "N-glycan structures of human transferrin produced by Lymantria dispar (gypsy moth) cells using the LdMNPV expression system," Glycobiology. 13(7):539-548.
Fryer et al. (2005) "Three decades of fish cell culture: a current listing of cell lines derived from fishes," J. Tissue Culture Methods. 16:87-94.
Hara et al. (1989) "Determination of mono-O-acetylatedN-acetylneuraminic acids in human and rat sera by fluorometric high-performance liquid chromatography," Analytical Biochemistry. 179(1):162-166.
Huang et al. (2001) "Microscale nonreductive release of O-linked glycans for subsequent analysis through MALDI mass spectrometry and capillarly electrophoresis," Analytical Chemistry. 73:6063-6060.
International Search Report for PCT/US08/60355 (Jul. 29, 2008).
Itoh et al. (2002) "Structural analysis of a glycoprotein by liquid chromatography-mass spectrometry and liquid chromatography with tandem mass spectrometry—Application to recombinant human thrombomodulin," J. of Chromatography. 978(1-2):141-152.
O'Neill et al. (1996) "Enzymatic release of oligosaccharides from glycoproteins for chromatographic and electrophoretic analysis," Journal of Chromatography A. 720:201-215.
Ogier-Denis et al. (1988) "The processing of asparagine-linked oligosaccharides in HT-29 cells is a function of their state of enterocytic diferentiation. An accumulation of Man9, 8-G1cNAc2-Asn species is indicative of an impaired N-glycan trimming in undifferentiated cells," J. of Biological Chemistry. 263(13):6031-6936.
Prime et al. (1996) "Oligosaccharide sequencing based on exo- and endo-glycosidase digestion and liquid chromatographic analysis of the products," Journal of Chromatography A. 720:263-274.
Stamatos et al. (2004). "Desialylation of glycoconjugates on the surface of monocytes activates the extracellular signal-related kinases ERK 1/2 and results in enhanced production of specific cytokines," J. of Leukocyte Biology. 75(2):307-313.
Suzuki. (2006). "The regulatory roles of cell surface sialylation and N-glycans in human B cell lymphoma cell adhesion to galectin-1," International Journal of Oncology. 28(1):1019-6439.
Written Opinion of the International Seach Authority for PCT/US08/60355 (Jul. 29, 2008).
Yuan et al. (2005) "Isotope tag method for quantitative analysis of carbohydrates by liquid chromatography-mass spectrometry," J Chromatography A. 1067:145-152.
Pace, et al., "Characterization of Minor N-linked Glycans on Antibodies Using Endo H Release and MALDI-Mass Spectrometry," Analytical Letters, 42: 1711-1724, 2009.
Dennis et al., "Glycoprotein glycosylation and cancer progression," Biochimica et Biophysica Acta, 1473: 21-34, 1999.
Ferens-Sieczkowska et al., "Haptoglobin glycoforms in a case of carbohydrate-deficient glycoprotein syndrome," Glycoconjugate Journal, 16: 573-577, 1999.

* cited by examiner

*Primary Examiner* — Sean Aeder
(74) *Attorney, Agent, or Firm* — Choate, Hall & Stewart LLP; Brenda H. Jarrell; Rolando Medina

(57) ABSTRACT

The present disclosure provides methods for assessing the glycosylation of a target glycoprotein produced by a cell through analysis of cell-surface glycans on the cell. The present disclosure therefore teaches that glycosylation of cell surface proteins can serve as a proxy for glycosylation of other proteins.

22 Claims, 6 Drawing Sheets

Figure 1: Loss of Core Fucosylation on Expressed Antibody Glycoprotein Produced in Cell Culture Medium Containing an Elevated Glucosamine Concentration
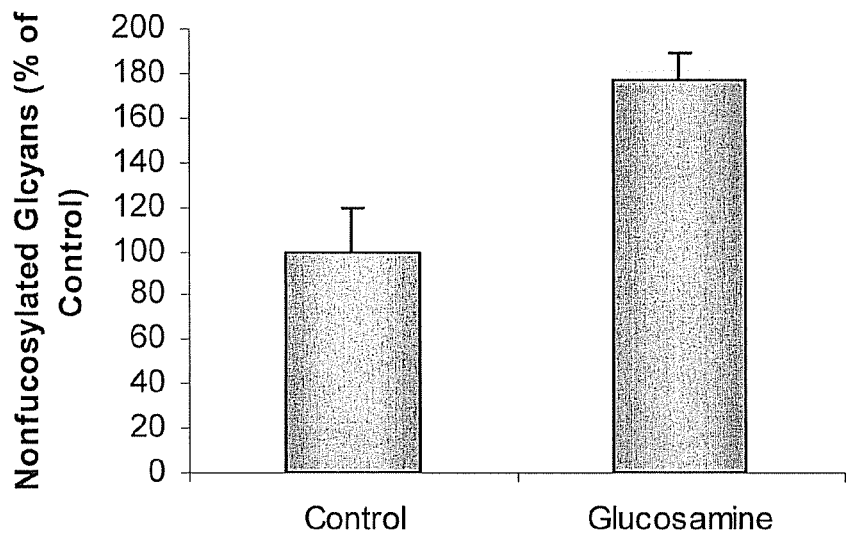
Figure 2: Loss of Core Fucosylation on Cell Surface Glycoproteins Produced in Cell Culture Medium Containing an Elevated Glucosamine Concentration
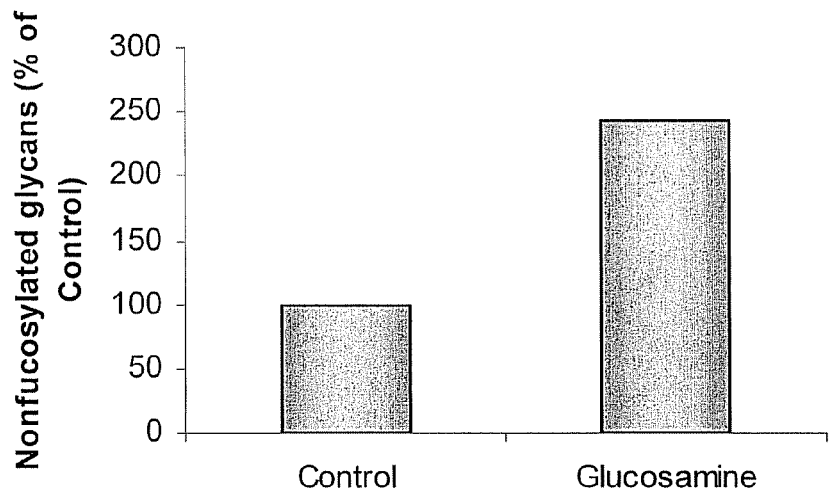

Figure 3A: Glycan Structures Of Cell Surface Glycoproteins Grown In Control Medium
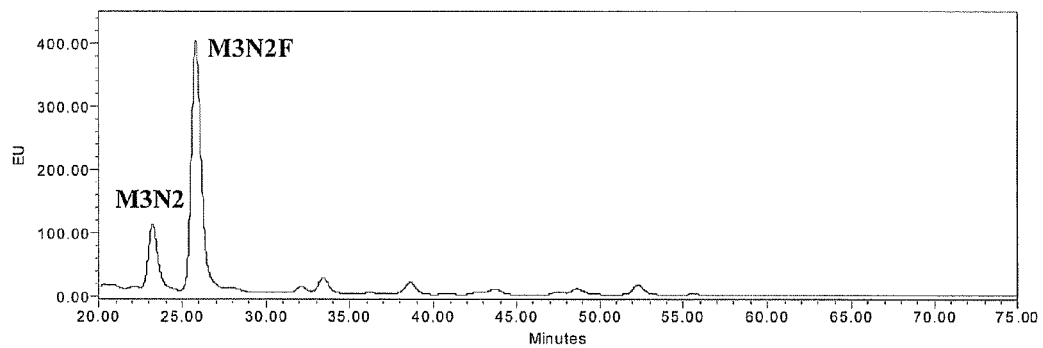
Figure 3B: Glycan Structures Of Cell Surface Glycoproteins Grown In Medium Containing An Elevated Glucosamine Concentration
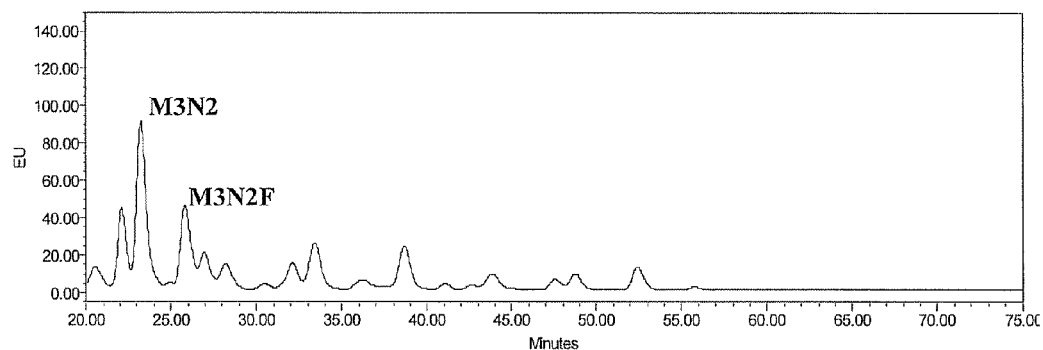

Figure 4: Liquid Chromatograpy Analysis of Sialic Acid Levels Of Expressed Recombinant Antibody and Cell Surface Glycoproteins
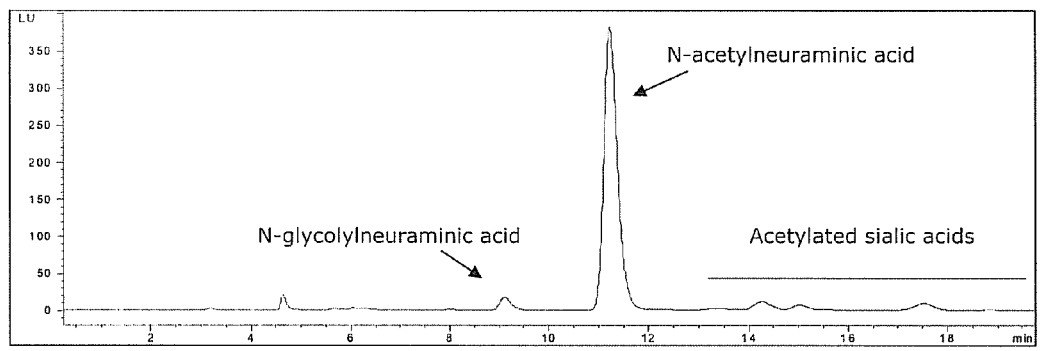

Figure 5: Sialic Acid Levels on Expressed Antibody Glycoprotein Produced in Cell Culture Medium Containing an Elevated N-Acetylmannosamine Concentration
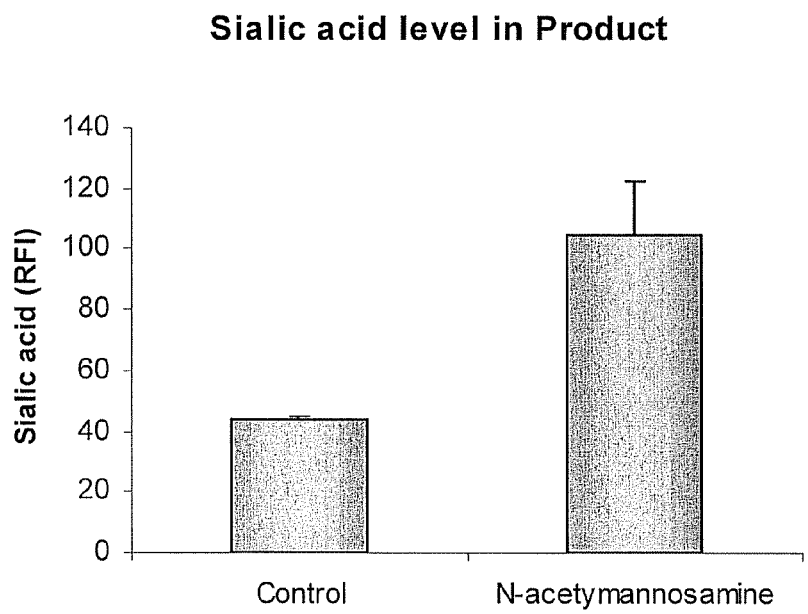
Figure 6: Sialic Acid Levels on Cell Surface Glycoproteins Produced in Cell Culture Medium Containing an Elevated N-Acetylmannosamine Concentration
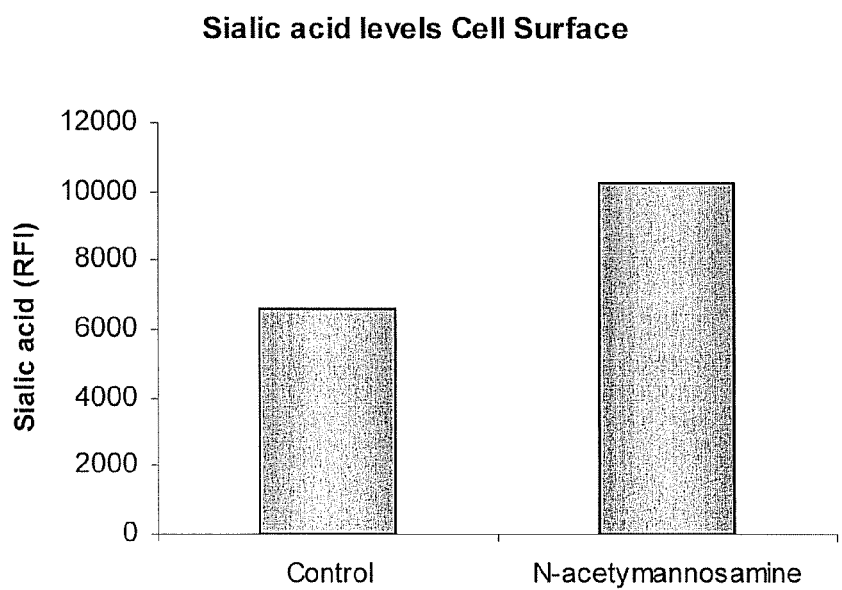

Figure 7: Sialic Acid Levels on Cell Surface Glycoproteins Produced in Cell Culture Medium Containing an Elevated N-Acetylmannosamine Concentration
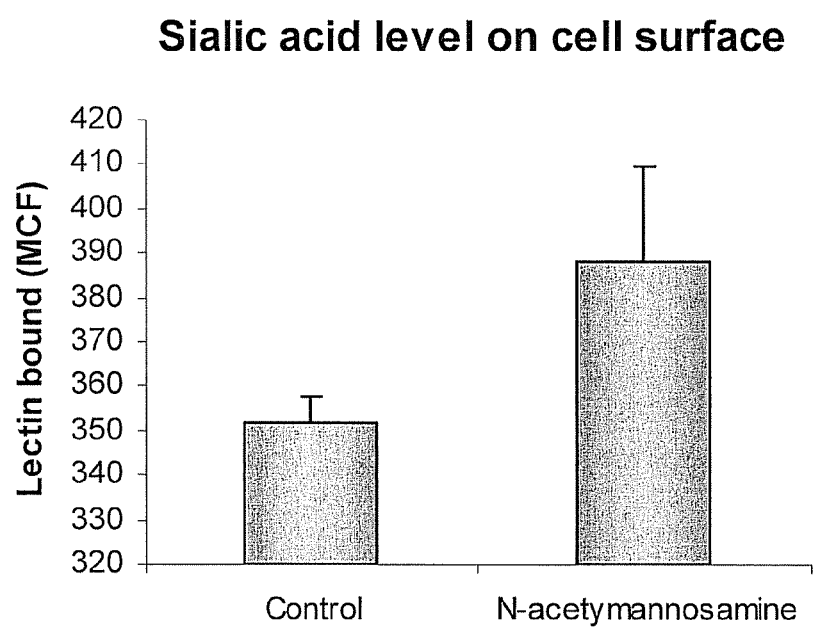

Figure 8: Cell Surface Sialic Acid Content Determined by Anion Exchange Chromatography of Cell Surface Glycans
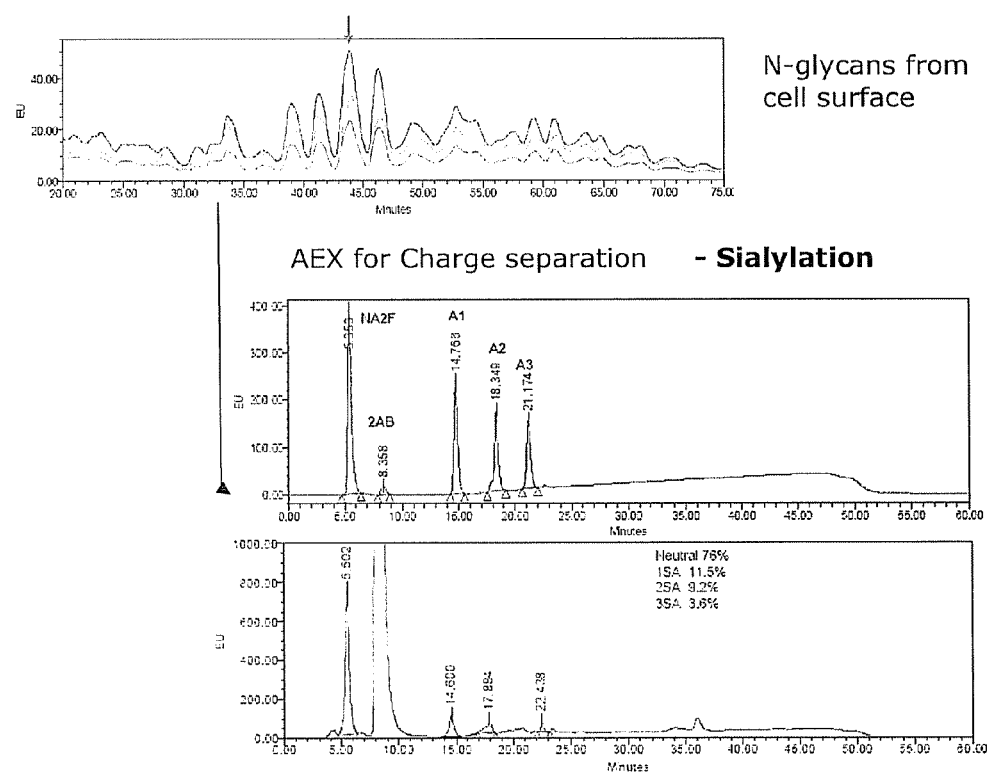

METHODS RELATED TO CELL SURFACE GLYCOSYLATION

This application is a national phase entry of international application serial number PCT/US08/60355, filed on Apr. 15, 2008, which claims priority to U.S. provisional application, Ser. No. 60/923,655, filed Apr. 16, 2007, the entire contents of both of which are incorporated herein by reference.

BACKGROUND

The glycosylation pattern of a glycoprotein often plays a significant role in the function of that glycoprotein. To give but a few examples, a glycoprotein's glycosylation pattern may affect its ability to fold correctly, its stability (e.g. resistance to proteolytic and/or other degradation), catalytic activity, pharmacodynamic and/or pharmacokinetic properties, and/or the ability of that glycoprotein to properly interact with other molecules. Alternatively or additionally, a glycoprotein's glycosylation pattern can affect transport and targeting of the glycoprotein. For example, a glycoprotein's glycosylation pattern may affect whether the glycoprotein remains intracellular (including, e.g., the correct targeting of the glycoprotein to the proper subcellular compartment or compartments), whether the glycoprotein will be membrane-bound and/or whether the glycoprotein will be secreted from the cell. For these reasons, it is important to be able to identify and/or characterize glycoprotein glycosylation patterns.

SUMMARY

The disclosure is based, in part, on the recognition that cell surface glycans can provide information about the state of the cell, e.g., as reflected in the glycosylation of proteins produced by the cell. In particular, it has been found that cell surface glycans can provide information about the glycosylation status of a glycoprotein produced (and optionally secreted) by the cell. Thus, one need not isolate a target protein from a cell in order to obtain information about its glycosylation status. Rather, glycosylation of one or more proteins or lipids on the cell surface can be evaluated to indirectly reveal one or more aspects of the glycosylation of a target protein. This can simplify and facilitate analysis of target protein glycosylation.

Among other things, the present disclosure provides methods in which cell-surface glycans are analyzed on cells that produce at least one target glycoprotein. Detection of the cell surface glycans serves as a proxy for detection of glycosylation on the target glycoprotein (that is, the detected glycans are not on or from the target glycoproteins). In many embodiments, the target glycoprotein is a non-cell-surface glycoprotein. For example, the target glycoprotein is soluble or secreted from the cell. In such embodiments, detection of cell-surface glycans serves as a proxy for determination of particular glycan structures on the produced non-cell-surface glycoprotein.

In certain embodiments, the present disclosure provides methods in which a cell that produces a glycoprotein of interest (e.g., a non-cell-surface glycoprotein or any other glycoprotein other than one whose associated glycans are being directly analyzed) is cultured under conditions that allow expression of the glycoprotein of interest and then is contacted with one or more reagents that detect glycosylation of a cell-surface glycan that is not part of the glycoprotein of interest. Typically, such methods will not include a step of isolating the glycoprotein of interest. Furthermore, in many embodiments, the steps do not include any direct analysis of the glycoprotein of interest. Thus, in such embodiments, analysis of the cell-surface glycan is used as a proxy to assess glycosylation of the target glycoprotein.

In some embodiments of the disclosure, the relevant cell is a mammalian cell, e.g., a CHO cell. In some embodiments of the disclosure, the target glycoprotein is a therapeutic glycoprotein; in some embodiments, the target glycoprotein comprises an antibody or antibody fragment.

In some aspects, the disclosure provides methods of identifying a glycosylation property of a glycoprotein produced by a cell by evaluating a property of a cell surface glycan of the cell (e.g., a cell surface glycan on a glycoprotein or glycolipid on the surface of the cell). In other aspects, a cell surface glycan property can correlate more generally with the state of the cell, e.g., with the cell's viability, morphology, density, or other property that may be affected by different process conditions, e.g., in a process for culturing the cell, e.g., in a process to produce a glycoprotein product from a cell. Thus, embodiments of the disclosure can be used in a variety of different contexts, e.g., among other things, cell surface glycans can be evaluated in order to:

(a) assess or predict glycosylation characteristics of a glycoprotein product, e.g., a therapeutic glycoprotein product, (b) monitor glycoprotein product quality (e.g., glycan structure) during one or more steps in a process for producing the glycoprotein product, (c) detect changes in process conditions in a process for producing a glycoprotein product, (d) provide information about (e.g., to compare) different batches of a glycoprotein preparation, (e) provide information about (e.g., to compare) cell status or glycoprotein product status during different steps in a process for producing the glycoprotein product, (f) to provide information about (e.g., to compare) cell status or glycoprotein product status during the same step in a plurality of processes for producing the glycoprotein product; and/or (g) to provide information about (e.g., to compare) glycosylation characteristics of a glycoprotein product produced by two or more cells or cell populations (e.g. clonal populations derived from single cells selected from an initial cell population) grown under similar or identical conditions.

BRIEF DESCRIPTION OF THE DRAWING

FIG. 1 shows core fucosylation levels on an expressed, non-cell-surface antibody glycoprotein produced in cell culture medium with or without elevated glucosamine supplementation FIG. 2 shows core fucosylation levels on cell surface glycoproteins produced in cell culture medium with or without elevated glucosamine supplementation FIGS. 3A-B shows glycan structures of cell-surface glycoproteins grown in control medium (FIG. 3A) or in medium containing an elevated glucosamine concentration (FIG. 3B).

FIG. 4 shows liquid chromatography analysis of sialic acid levels of expressed (non-cell surface) recombinant antibody and cell-surface glycoproteins.

FIG. 5 shows sialic acid levels on expressed antibody glycoprotein produced in cell culture media with or without an elevated N-acetylmannosamine concentration, as measured by DMB labeling and HPLC FIG. 6 shows sialic acid levels on cell-surface glycoproteins in cell culture media with or without an elevated N-acetylmannosamine concentration, as measured by DMB labeling and HPLC.

FIG. 7 shows sialic acid levels on cell-surface glycoproteins produced in cell culture media with or without an elevated N-acetylmannosamine concentration, as measured by sialic acid-specific lectin binding and flow cytometry.

FIG. 8 shows cell surface sialic acid content determined by anion exchange chromatography of cell surface glycans. Migration of the neutral (NA2F), monosialylated (A1), disialylated (A2), or trisialylated (A3) standards are indicated on the top chromatogram. The lower chromatogram illustrates representative data from cell surface glycans of CHO cells, and relative percentages.

DEFINITIONS

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample", as used herein, refers to any solid or fluid sample obtained from, excreted by or secreted by any living cell or organism, including, but not limited to, tissue culture, bioreactor sample, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell.

Cell-surface glycan: A "cell-surface glycan" is a glycan that is present on the exterior surface of a cell. In many embodiments of the present disclosure, a cell-surface glycan is covalently linked to a polypeptide as part of a cell-surface glycoprotein. A cell-surface glycan can also be linked to a cell membrane lipid.

Correlating: The term "correlating", as used herein, refers to the establishment of a predictable relationship between two things. In embodiments described herein, a glycosylation pattern (or a characteristic thereof) on the surface of a cell is correlated with a glycosylation pattern (or a characteristic thereof) of a target glycoconjugate (e.g., glycoprotein) produced by the cell. The correlated patterns (or characteristics) need not be identical with one another so long as one can be predicted from the other. Once a correlation is established, it can be recorded, for example, in a written record or can otherwise be affixed in a medium or memory source (e.g., a computer-readable medium or computer memory bank or disc). Detection of a correlated glycosylation pattern (or characteristic thereof) can then involve reference to the written or affixed record, or to a comparator experiment confirming the correlation, etc. Such a comparator experiment may be performed simultaneously with an assessment of glycosylation pattern (or characteristic thereof), or can be a historical or future experiment.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below).

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform", is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform".

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments, sugar moieties may include sulfate and/or phosphate groups. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycoprotein preparation: A "glycoprotein preparation", as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell surface glycans, or a "surface glycosylation pattern". As used herein, a "surface glycosylation pattern" may refer to the pattern of glycans (or "glycosylation pattern") that exists on the extracellular domain of a single cell surface glycoprotein and/or glycolipid of interest. Additionally or alternatively, a "surface glycosylation pattern" may refer to the pattern of glycans (or "glycosylation pattern") that exists on the extracellular domain of a plurality of cell surface glycoproteins and/or glycolipids. In certain embodiments, a "surface glycosylation pattnern" describes the pattern of glycans (or "glycosylation pattern") that exists on the entire complement of cell surface glycoproteins and/or glycolipids. Based on context, those of ordinary skill in the art will readily understand whether "surface glycosylation pattern" refers to the glycosylation pattern of a single cell surface glycoprotein and/or glycolipid or to the glycosylation pattern of a plurality of cell surface glycoproteins and/or glycolipids. A glycosylation pattern can be characterized by, for example, the identities of glycans, amounts (absolute or relative) of individual glycans or glycans of particular types, degree of occupancy of glycosylation sites, etc., or combinations of such parameters.

N-glycan: The term "N-glycan," as used herein, refers to a polymer of sugars that has been released from a glycoconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exists, but is typically based on the common core pentasaccharide $(Man)_3(GlcNAc)$ (GlcNAc).

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D galactosamine (GalNAc) or via N-acetyl-D-glucosamine (GlcNAc) to the hydroxyl group of L serine (Ser) or Lthreonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Phosphorylation: As used herein, the term "phosphorylation" refers to the process of covalently adding one or more phosphate groups to a molecule (e.g., to a glycan).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sialic acid: The term "sialic acid," as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the car boxyl group tends to dissociate a proton at physiological pH. Exemplary deprotonated sialic acids are as follows:

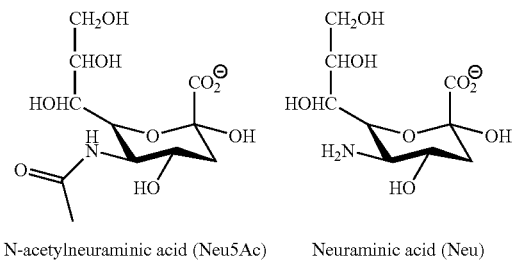

N-acetylneuraminic acid (Neu5Ac)   Neuraminic acid (Neu)

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. To give but one particular example, when it is said that a treatment does not "substantially" rupture the cell membranes, it is meant to indicate that all or most of the cell membranes remain intact during and after the treatment, for example so that intracellular glycoproteins or glycopeptides are thus not released from the cells. In certain embodiments, the term "substantially", as applied to unruptured cell membranes, refers to condition wherein 15%, 10%, 9%, 8%, 7%, 6%, 5%, 4%, 3%, 2%, 1%, or fewer of the cells subjected to a particular treatment exhibit measurable ruptured cell membranes. In certain embodiments, the term "substantially", as applied to unruptured cell membranes, refers to condition wherein none of the cells subjected to a particular treatment exhibit measurable ruptured cell membranes.

DETAILED DESCRIPTION OF CERTAIN PREFERRED EMBODIMENTS

As described herein, the present disclosure relates to detection of glycan structures present on the surface of cells, the presence, identity, and/or distribution (e.g., relative amounts) of which reveal information about the state of the cell, e.g., information about the glycosylation state and/or characteristics of one or more non-cell-surface glycoproteins produced by the cells. That is, in one aspect of the disclosure, cell-surface glycans act as a proxy for the determination of glycan structures and/or glycosylation patterns found on non-cell-surface glycoproteins. In some embodiments of the disclosure, the non-cell-surface glycoprotein is a therapeutic glycoprotein. In some such embodiments, the cell has been engineered to express the therapeutic glycoprotein, and/or to express the therapeutic protein at predetermined level or under predetermined conditions.

Cell-Surface Glycans

Many different types of cells glycosylate at least some of the proteins and/or lipids that they produce, and several different mechanisms exist for such glycosylation. In general, however, oligosaccharide chains are linked to a polypeptide chain (i.e., to a protein) and/or to a lipid in the endoplasmic reticulum and in the Golgi apparatus via either N-linkages or O-linkages.

N-Linked Glycosylation

Typically, N-linked oligosaccharide chains are added to a protein in the lumen of the endoplasmic reticulum (see Molecular Biology of the Cell, by Alberts et al., 1994, incorporated herein by reference). Specifically, an initial oligosaccharide (typically 14-sugar) is added to the amino group on the side chain of an asparagine residue contained within the target consensus sequence of Asn-X-Ser/Thr, where X may be any amino acid except proline. The structure of this initial oligosaccharide is common to most eukaryotes, and contains 3 glucose, 9 mannose, and 2 N-acetylglucosamine residues. This initial oligosaccharide chain is usually trimmed by specific glycosidase enzymes in the endoplasmic reticulum, resulting in a short, branched core oligosaccharide composed of two N-acetylglucosamine and three mannose residues.

N-glycans can be subdivided into three distinct groups called "high mannose type", 'hybrid type', and 'complex type', with a common pentasaccharide core (Man (alpha1,6)-(Man(alpha1,3))-Man(beta1,4)-GlcpNAc(beta 1,4)-GlcpNAc(beta 1,N)-Asn) occurring in all three groups.

After initial processing in the endoplasmic reticulum, the glycoprotein is then transported to the Golgi where further processing may take place. If the glycan is transferred to the Golgi before it is completely trimmed to the core pentasaccharide structure it results in a "high-mannose glycan".

Additionally or alternatively, one or more monosaccharides units of N-acetylglucosamine may be added to the core mannose subunits to form a 'complex glycan'. Galactose may be added to the N-acetylglucosamine subunits, and sialic acid subunits may be added to the galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

'Hybrid glycans' comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

O-Linked Glycosylation

O-linked oligosaccharide chains are added to specific serine or threonine residues in polypeptide chains. The transfer of the first sugar residue, which in many instances is an N-acetylgalactosamine, typically begins in the endoplasmic reticulum and is completed in the Golgi apparatus. The residues of an O-linked oligosaccharide are added one at a time and the addition of each residue is catalyzed by a specific enzyme. In contrast to N-linked glycosylation, the consensus amino acid sequence for O-linked glycosylation is less well defined.

Target Glycoproteins

Techniques of the present disclosure may be applied to assess the glycosylation state of any non-cell-surface glycoprotein or any other glycoprotein of interest other than one whose glycans are being directly analyzed or produced by a particular cell or population of cells. The identity of the non-cell-surface glycoprotein of interest is not intended to limit the present disclosure. In most embodiments, however, the cell or cells is/are known to produce a particular glycoprotein of interest (the "target" glycoprotein), whose glycosylation state is to be assessed.

In many embodiments, the target glycoprotein of interest is one that is not naturally produced by the cell; rather, the cell has been engineered to produce it. In some embodiments, the target glycoprotein is one that is naturally produced by the cell, but the cell has been engineered to produce it at an elevated level and/or under predetermined conditions (e.g., in the presence of an inducing agent, etc.)

In many embodiments, a target glycoprotein has therapeutic activity when administered to animals (e.g., mammals such as humans). To give but a few examples, erythropoietins, interferons, blood-clotting factors, colony stimulating factors, a variety of antibodies, and certain enzymes are all glycoproteins that are currently produced in engineered cell lines as biopharmaceutical agents. In some embodiments of the present disclosure, glycans on the surface of cells that produce one or more of these agents are assayed as described herein in order to assess or monitor glycosylation of the agent. One of ordinary skill in the art will be aware of other commercially relevant glycoproteins that can be expressed industrially (e.g., in production bioreactors) for therapeutic and other purposes. The present disclosure provides methods for monitoring the glycosylation patterns of such commercially relevant glycoproteins.

Representative commercially available glycoprotein products include, for example:

| Protein Product | Reference Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex-human | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |

-continued

| Protein Product | Reference Drug |
|---|---|
| filgrastim | Neupogen ® |
| fanolesomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| daclizumab | Zenapax ® |
| ibritumomab tiuxetan | Zevalin ™ |
| Somatotropin | Zorbtive ™ (Serostim ®) |

As will be appreciated by those of ordinary skill in the art, the glycosylation patterns of such therapeutic glycoproteins can potentially affect their therapeutic properties. The present disclosure provides technologies that allow investigators to assess glycosylation of these proteins as they are produced in cells without requiring isolation of the proteins themselves. As is discussed further below, the present disclosure therefore provides, among other things, real-time assessment of product quality for therapeutic glycoprotein products as the glycoproteins are being produced.

Those of ordinary skill in the art will appreciate that the present disclosure is not limited to assessment of glycosylation on the above-listed glycoproteins, or indeed on therapeutic glycoproteins, or on glycoproteins whose expression (and/or degree or timing of expression) has been engineered in a cell. These represent merely certain particular embodiment of the present disclosure; those of ordinary skill in the art will appreciate, however, that the principles of the disclosure apply to any target glycoprotein.

Production of Target Glycoproteins in Cells

Those of ordinary skill in the art will readily appreciate that glycoproteins whose glycosylation is to be monitored as described herein can be produced in any of a variety of cells and/or cell lines. Indeed, any cell that glycosylates at least some of its proteins can be utilized and grown under any conditions that allow such glycosylation to occur. Suitable cells include, but are not limited to, mammalian cells, avian cells, fish cells, insect cells, plant cells, fungal cells, bacterial cells, and hybrid cells. In some embodiments, the cells have been engineered (e.g., genetically and/or chemically) to have one or more glycosylation characteristics more similar to human cells.

Exemplary mammalian cells that can be used in accordance with the present disclosure include, but are not limited to, Chinese hamster ovary (CHO) cells, HeLa cells, Madin-Darby canine kidney (MDCK) cells, baby hamster kidney (BHK cells), NSO cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

Exemplary fish cell lines that can be used in accordance with the present disclosure include, but are not limited to, ZF4 cells, AB9 cells, GAKS cells, OLF-136 cells, CAEP cells, CAF cells, OLHE-131 cells, OLME-104 cells, ULF-23 cells, BRF41 cells, Hepa-E1 cells, Hepa-T1 cells, GEM-81 cells, GEM-199 cells, GEM-218 cells, GAKS cells, D-11 cells, R1 cells, RTG-2 cells, RTO cells, and TPS cells. A more complete list can be found in Fryer and Lannan, 2005, "Three decades of fish cell culture: a current listing of cell lines derived from fishes," *J. Tissue Culture Methods*, 16:87-94.

Exemplary insect cell lines that can be used in accordance with the present disclosure include, but are not limited to, SFM cells, Sf21 cells, Sf9 cells, Schneider cells, S2 cells, T.ni cells, SES-MaBr-1 cells, SES-MaBr-3 cells, NIAS-MB-25 cells, NIAS-MaBr-92 cells, FRISpIm-1229 cells, SES-MaBr-4 cells, NIAS-LeSe-11 cells, TUAT-SpLi-221 cells, NIAS-PX-64 cells, NIAS-MB-32 cells, NIAS-MaBr-93 cells, SES-MaBr-5 cells, BM-N cells, NIAS-PX-58 cells, MBHL-2 cells, and MBHL-3 cells.

Those of ordinary skill in the art will recognize that this is an exemplary, not a comprehensive, listing of various cells that may be used in accordance with the present disclosure. Other cells may be advantageously utilized to produce a target glycoprotein. Such cells may be in culture or in the context of a tissue, organ, or organism.

Those skilled in the art will also appreciate that a variety of expression systems and vectors may be used in order to express a protein of interest within cells or cell lines used in accordance with the present disclosure (e.g., see *Molecular cloning: A Laboratory Manual*, Ed. by Sambrook, CSHL Press, 2002).

Also, any of a variety of cell culture media, including complex media and/or serum-free culture media, that are capable of supporting growth of the one or more cell types or cell lines may be used in accordance with the present disclosure. Typically, a cell culture medium contains a buffer, salts, energy source, amino acids (e.g., natural amino acids, non-natural amino acids, etc.), vitamins and/or trace elements. Cell culture media may optionally contain a variety of other ingredients, including but not limited to, carbon sources (e.g., natural sugars, non-natural sugars, etc.), cofactors, lipids, sugars, nucleosides, animal-derived components, hydrolysates, hormones/growth factors, surfactants, indicators, minerals, activators/inhibitors of specific enzymes, and organics (e.g., butyrate, which induces apoptosis, which releases glycosylases, often slows down growth rate of cell, which changes glycosyltransferase levels, which can result in more mature glycosylation; and results in change in energy of cell; chloroquin, which affects intracellular pH; betaine, an osmoprotectant; ammonia, which alters intracellular pH levels and which can change glycosyl transferase efficiency; etc.), and/or small molecule metabolites (e.g., CMP-sialic acid, glucosamine, non natural sugar derivatives, etc.). Cell culture media suitable for use in accordance with the present disclosure are commercially available from a variety of sources, e.g., ATCC (Manassas, Va.).

In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium. As will be understood by those of ordinary skill in the art, when defined medium that is serum-free and/or peptone-free is used, the medium is typically highly enriched for amino acids and trace elements (see, for example, U.S. Pat. No. 5,122,469 to Mather et al., and U.S. Pat. No. 5,633,162 to Keen et al.).

Different cell culture media may affect the glycosylation pattern of glycoproteins expressed in the media. For example, a given cell culture medium may result in production of glycoproteins with an increased glycosylation pattern, a decreased glycosylation pattern, or an altered glycosylation (e.g., representing an increase in certain glycans and a decrease in others). One of ordinary skill in the art will be aware of and will be able to choose one or more suitable cell culture media for use in growing cells whose cell-surface glycans are to be analyzed using certain methods of the present disclosure.

In some embodiments, cells are cultured in batch culture, fed batch culture, perfusion culture, static suspension (e.g., roller bottles, T flasks, microcarriers, T150, etc.), and/or on shakers.

Cells that produce at least one non-cell-surface glycoprotein (i.e., target glycoprotein) according to the present disclosure can be grown under any of a variety of cell culture conditions.

In some embodiments, cells are cultured under cell culture conditions such that the target glycoprotein is expected to exhibit a desired glycosylation pattern. In some embodiments, one or more cell culture conditions are controlled and/or modified in order to produce the target glycoprotein with a more desirable glycosylation patterns. Such cell culture conditions that can be controlled or modified include, but are not limited to, pH, $CO_2$ levels, oxygen levels, culture agitation rate, redox conditions, culture temperature, cell density, density of seed culture, duration of culture, reactor design, sparge rate, and/or osmolarity.

Any of a variety of methods can be used to isolate cells from the cell culture medium, if desired. In certain embodiments, cells are grown in a suspension culture. In such embodiments, cells may be purified from the cell culture medium by one or more cycles of centrifugation and washing (e.g., with a physiological suitable washing solutions such as phosphate-buffered saline).

In certain embodiments, cells are grown in an adhesion culture. In such embodiments, cells may be purified from the cell culture medium by first releasing them from the culture surface. For example, cells may be released from the culture surface by subjecting them to EDTA. Those of ordinary skill in the art will be aware of other suitable agents that can be used to release adherent cells from the culture surface. After release, cells may be purified by one or more cycles of centrifugation and washing (e.g., with a physiological suitable washing solutions such as phosphate-buffered saline). As with cells grown in suspension culture, care should be taken not to centrifuge the cells with too much force in order to avoid unnecessary cell breakage.

Analysis of Cell-Surface Glycans

Any suitable technique may be utilized to detect glycans on a cell surface according to the present disclosure. Glycans can be detected and/or analyzed on cells, for example while still part of a glycoprotein produced by a cell. For example, according to certain embodiments, glycans are detected and/or analyzed on cells in the absence of protease or glycosidase treatment. Alternatively or additionally, glycans can be released from cells and then detected and/or analyzed. Glycans can be released from cells by subjecting cells to one or more proteases, glycosidases, or both. For example, a glycopeptide can be liberated from a cell by subjecting the cell to one or more proteases such as, without limitation, proteases described herein, which liberated glycopeptide is subjected to one or more glycosidases, such as, without limitation, glycosidases described herein. As another non-limiting example, glycans can be released from the cell directly by subjecting the cell to glycosidase treatment, without subjecting the cell to protease treatment. Certain representative analytical techniques are addressed in more detail below, but are not intended to limit the scope of the present disclosure.

Release of Glycopeptides

In certain embodiments, of the present disclosure, one step involved in analyzing cell-surface glycans is liberating such glycans from the surface of the cell. Among the several advantages offered by such embodiments is the fact that a highly pure population of cell-surface glycans can be obtained without significant contamination by glycans that are primarily found inside the cell. For example, using certain methods of the present disclosure, lysis of cells is substantially avoided when cell-surface glycans are liberated from the cell. Additionally or alternatively, certain methods disclosed herein offer significant reductions in the number and/or difficulty of manipulation steps as compared to currently available methods.

In certain embodiments, cell-surface glycoproteins are liberated from the cell surface by subjecting the cell to one or more proteases. Proteases cleave amide bonds within a polypeptide chain. Several classes of proteases exist including both chemical and enzymatic agents. Proteolytic enzymes include, for example, serine proteases, threonine proteases, cysteine proteases, aspartic acid proteases, metalloproteases, and glutamic acid proteases. Non-limiting examples of specific proteolytic enzymes that can be used in accordance with the present disclosure include trypsin, chymotrypsin, elastase, subtilisin, proteinase K, pepsin, ficin, bromelin, plasmepsin, renin, chymosin, papain, a cathepsin (e.g. cathepsin K), a caspase (e.g. CASP3, CASP6, CASP7, CASP14), calpain 1, calpain 2, hermolysin, carboxypeptidase A or B, matrix metalloproteinase, a glutamic acid protease, and/or combinations thereof. Those of ordinary skill in the art will be aware of a number of other proteases that can be used in accordance with the present disclosure to release a glycoprotein from the surface of a cell.

Current methods of analyzing cellular glycoproteins, even when explicitly stated to be targeting cell surface glycans, are typically not particularly selective for cell surface glycans. For example, current methods typically employ one or more harsh detergents to extract membrane proteins, after which free sugars are dialyzed away before treatment with agents that remove glycan structures from proteins or polypeptides. Under such conditions, glycan preparations are contaminated by intracellular glycans, e.g., from the endoplasmic reticulum and/or Golgi apparatus. Such intracellular glycans are typically immature, high-mannose glycans. Thus, their inclusion can skew the analysis of glycan structures associated with cell surface glycoproteins.

In some embodiments of the present disclosure, analysis of cell surface glycans involves use of detergents to release cell surface glycoproteins from membranes. In some embodiments of the present disclosure, however, detergent treatment is minimized or avoided altogether in favor of strategies that minimize disruption of cell membranes. For example, in some embodiments, at least 80%, 85%, 90%, 95%, 96%, 97%, 98%, 99%, or more of the cell membranes remain intact (e.g., as monitored by trypan blue exclusion). Such methods are advantageous, among other things, because the can reduce or eliminate contamination from immature, high-mannose glycoproteins that are present inside the cell.

In certain embodiments of the present disclosure, glycans (in the form of glycopeptides) are liberated from a cell surface by subjecting the cell to one or more proteases. In certain embodiments, cells are subjected to one or more proteases under conditions that minimize disruption of the cell membrane. In some embodiments of the disclosure, glycans are liberated from a cell surface by subjecting the cell to one or more proteases for a limited period of time in order to avoid substantial lysis of the cell membrane. In certain embodiments, a cell is subjected to one or more proteases for a sufficiently limited time such that substantial lysis of the cell membrane does not occur.

For example, a cell may be subjected to one or more proteases for a period of time that is less than about 15, 14, 13, 12, 11, 10, 9, 8, 7, 6, 5, 4, 3, 2, or 1 minute. In certain embodiments, a cell is subjected to one or more proteases for a period of time that is more than 15 minutes so long as substantial lysis of the cell membrane does not occur. For example, a sufficiently low concentration of protease(s), a sufficiently low temperature and/or any of a variety of other factors or conditions may be employed such that the overall protease activity is decreased to a point where substantial lysis of the cell membrane does not occur. Those of ordinary skill in the art will be aware of and will be able to employ factors or conditions that ensure that substantial lysis of the cell membrane does not occur.

In certain embodiments of the present disclosure, at least about 50%, 60%, 70%, 80%, 90%, 91%, 92%, 93%, 94%, 95%, 96%, 97%, 98%, 99% or more of cell surface glycans are released from cells, for example by treatment with a protease. To give but one specific example, the present disclosure demonstrated, for instance, that cleavage with trypsin for 15 min at 37° C. results in release of greater than 50% of the cell surface glycans In certain embodiments, cell surface glycans are liberated by subjecting a cell to one or more proteases (e.g., proteolytic enzymes) at a concentration of at least about 0.1 mg/mL. In certain embodiments, cell surface glycans are liberated by subjecting a cell to one or more proteases (e.g., proteolytic enzymes) at a concentration of less than about 2.0 mg/mL. In certain embodiments, cell surface glycans are liberated by subjecting a cell to one or more proteases (e.g., proteolytic enzymes) at a concentration of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 5.0, 6.0, 7.0, 8.0, 9.0, 10.0 mg/mL or higher.

In certain embodiments, cell surface glycans are liberated by subjecting a cell to a plurality of proteases. For example, a cell may be subjected to 2, 3, 4, 5, 6, 7, 8, 9, 10, or more proteases to liberate cell surface glycans. Such a plurality of proteases may be administered to the cell simultaneously and/or sequentially. In certain embodiments, cell surface glycans are liberated by subjecting a cell to a plurality of proteases simultaneously, after which the liberated glycans (in the form of glycopeptides) are purified away from the cell.

In certain embodiments, cell surface glycans are liberated by subjecting a cell to a first protease (or plurality of first proteases) for a first period of time, after which the cell is subjected to a second protease (or plurality of second proteases) for a second period of time. Prior to treatment with the second protease, the first protease may optionally be removed and/or inactivated. By way of example, the first protease may be inactivated incubating the protease at a temperature for a time sufficient to inactivate it. Additionally or alternatively, the first protease may be inactivated by incubating it with an inhibitor that is specific to the protease (e.g. an antibody or other molecule that specifically binds the first protease and inhibits its catalytic activity). Other methods of inactivating the first protease will be known to those of ordinary skill in the art. In the case where the first protease is inactivated by incubating it with a specific inhibitor, it will be appreciated that the presence of the inhibitor should not substantially inhibit the activity of the second protease.

In certain embodiments the protease(s) are removed and/or inactivated prior to release of glycans. By way of example, a protease may be inactivated incubating the protease at a temperature for a time sufficient to inactivate it. Alternatively or additionally a protease may be inactivated by incubating with an inhibitor or antibody or other molecule that specifically binds to the protease and inhibits its catalytic activity.

Release of Glycans

In certain embodiments of the present disclosure, cell-surface glycans are cleaved prior to being analyzed. For example, in certain embodiments, one or more glycan structures are cleaved from cell surface glycopeptides after the cell surface glycopeptides have been liberated from the cell (e.g., through treatment with proteases, as described in more detail above). In certain embodiments, one or more glycan structures are cleaved from cell-surface glycoproteins that have not been liberated from the cell.

In certain embodiments, one or more glycan structures are released through the use of an enzyme or plurality of enzymes that recognizes and cleaves the glycan structures. Any of a variety of glycosidic and other enzymes that cleave glycan structures from cell-surface glycoproteins may be used in accordance with the present disclosure. Several examples of such enzymes are reviewed in R. A. O'Neill, *Enzymatic release of oligosaccharides from glycoproteins for chromatographic and electrophoretic analysis*, J. Chromatogr. A 720, 201-215. 1996; and S. Prime, et al., *Oligosaccharide sequencing based on exo- and endo-glycosidase digestion and liquid chromatographic analysis of the products*, J. Chromatogr. A 720, 263-274, 1996, each of which is incorporated herein by reference in its entirety. In certain embodiments, the enzyme PNGase F (Peptide N-Glycosidase F) is used to remove glycans from a glycopeptide or glycoprotein. PNGase F is an amidase that cleaves the amide bond between the innermost GlcNAc and asparagine residues of high mannose, hybrid, and complex oligosaccharides from N-linked glycoproteins. Additionally or alternatively, in certain embodiments, the enzymes PNGase A, O-glycanase, and/or Endo-H are used to remove glycans.

To improve the accessibility of the glycosylation site to a cleavage enzyme, most glycoproteins require a protein denaturation step. Typically, this is accomplished by using detergents (e.g., SDS) and/or disulfide-reducing agents (e.g., beta-mercaptoethanol), although methods of denaturing a glycoprotein for use in accordance with the present disclosure are not limited to the use of such agents. For example, exposure to high temperature can be sufficient to denature a glycoprotein such that a suitable enzyme for cleaving glycan structures is able to access the cleavage site. In certain embodiments, a glycoprotein is denatured by incubating the glycoprotein at temperature of 80, 81, 82, 83, 84, 85, 86, 87, 88, 89, 90, 91, 92, 93, 94, 95, 96, 97, 98, 99, 100 degrees Celsius, or higher for a period of time sufficient to denature the glycoprotein.

In certain embodiments, a combination of detergents, disulfide-reducing agents, high temperature, and/or other agents or reaction conditions is employed to denature a glycoprotein. Those of ordinary skill in the art will be aware of suitable conditions, incubation times, etc. that will be sufficient to denature a glycoprotein. It is noted that oligosaccharides located at conserved Fc sites in immunoglobulin G (IgG) are easily cleaved by PNGase F. Thus, a protein denaturation step is typically not required for IgG molecules when this enzyme is used. PNGase F is also capable of removing oligosaccharides in dilute ammonium hydroxide solution, is stable in 2.5M urea at 37C for 24 h, and still possesses 40% of its activity in 5 M urea. Thus, PNGase F has the advantage that it is capable of cleaving glycans from glycoproteins under certain denaturation conditions.

Other suitable enzymes that can be used to cleave glycan structures from glycoproteins in accordance with the present disclosure include, but are not limited to, PNGase A, O-glycanase and/or Endo-H. Those of ordinary skill in the art will be aware of other suitable enzymes for cleavage of glycans from glycoproteins. In certain embodiments, a plurality of enzymes is used to cleave glycan structures from a glycoprotein. In certain embodiments, such a plurality of cleavage enzymes is administered simultaneously. In certain embodiments, such a plurality of cleavage enzymes is administered sequentially.

In certain embodiments, one or more glycan structures are cleaved from cell-surface glycoproteins through the use of an agent other than an enzyme. In certain embodiments, a chemical agent or plurality of chemical agents (e.g., exposure to an agent such as hydrazine, sodium borohydride, endoglycosidases, trifluoromethasenulfonic acid (TFMS), and/or beta-elimination, etc) can be used to cleave glycan structures from glycoproteins. For example, use of the chemical hydrazine has been successfully employed to cleave glycan structures. As another non-limiting example, it has been suggested that a mixture of ammonia-ammonium carbonate can be used for alkaline release of both the N- and O-linked oligosaccharides in their native form (see Y. Huang, et al., *Microscale nonreductive release of O-linked glycans for subsequent analysis through MALDI mass spectrometry and capillary electrophoresis*, Anal. Chem. 73, 6063-60, 2001, incorporated herein by reference in its entirety). Those of ordinary skill in the art will be aware of other suitable chemical agents that can be used in accordance with the present disclosure. In some cases, use of a chemical agent to cleave glycan structures from a glycoprotein results in protein degradation as well as cleavage. However, after cleavage, the glycan structure is often purified away from the protein component of the glycoprotein before analysis and/or characterization. In such situations, degradation of the protein component after treatment with a chemical agent is not detrimental to the practice of the present disclosure. In some cases, degradation of the protein component may even aid in the process of purifying the cleaved glycan structure(s).

In some embodiments, glycans that have been released from a glycoprotein and/or released from a cell surface can be digested with one or more exoglycosidases, and the structure and/or composition of the digestion products can be analyzed.

Exoglycosidases are enzymes which cleave terminal glycosidic bonds from the non-reducing end of glycans. They are typically highly specific to particular monosaccharide linkages and anomericity (a/(3). In some embodiments, neighboring branching patterns can affect exoglycosidase specificity. Exoglycosidase treatment usually results in glycans of standard antennary linkages being cleaved down to the pentasaccharide core (M3N2) containing 3 mannose and 2 glcNAc residues. However, unusually-modified species (e.g. antennary fucosylated species, high-mannose and hybrid glycans, lactosamine-extended glycans, sulfated or phosphorylated glycans, etc.) are resistant to exoglycosidase treatment and can be chromatographically resolved and quantified relative to the M3N2 pentasaccharide.

In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage. Exemplary exoglycosidases that can be used in accordance with the present disclosure include, but are not limited to, sialidase, galactosidase, hexosaminidase, fucosidase, and mannosidase. Exoglycosidases can be obtained from any source, including commercial sources (e.g. from QA-Bio, ProZyme, Roche, Sigma, NEB, EMD, Glyko, etc.). Alternatively or additionally, exoglycosidases can be isolated and/or purified from a cellular source (e.g. bacteria, yeast, plant, etc.).

In some embodiments, exoglycosidases (e.g. sialidases, galactosidases, hexosaminidases, fucosidases, and mannosidases) can be divided into multiple categories or "subsets." In some embodiments, the different subsets display different abilities to cleave different types of linkages. Table 1 presents some exemplary exoglycosidases, their linkage specificities, and the organism from which each is derived. One of ordinary skill in the art will appreciate that this is an exemplary, not a comprehensive, list of exoglycosidases, and that any exoglycosidase having any linkage specificity may be used in accordance with the present disclosure.

tially. In some embodiments, varying the identity of the exoglycosidases which are administered reveals information about glycan structure and/or composition. In some embodiments, varying the sequence in which multiple exoglycosidases are administered reveals information about glycan structure and/or composition.

In some embodiments, sequential digestion with multiple exoglycosidases reveals information about glycan structure and/or composition that is different from information revealed by simultaneous digestion with the same set of exoglycosidases. In some embodiments, sequential digestion with multiple exoglycosidases reveals information about glycan structure and/or composition that is the same information revealed by simultaneous digestion with the same set of exoglycosidases. For a more complete discussion of the utility of exoglycosidase digestion in the analysis of glycan structure, see co-pending U.S. provisional patent application U.S. Ser. No. 60/923,688, filed Apr. 16, 2007, by Parsons et al., entitled "CHARACTERIZATION OF N-GLYCANS USING EXOGLYCOSIDASES," which is incorporated herein by reference.

Glycan Analysis

Glycans may be analyzed by any technique including, for example, ligand binding, mass spectrometry, nuclear magnetic resonance, and/or other methodologies. A variety of

TABLE 1

Exoglycosidases

| Enzyme class | EC #* | Activity | Organism |
|---|---|---|---|
| α-Sialidase | 3.2.1.18 | α-2/3,6,8 (usually not linkage-specific) | *Arthrobacter ureafaciens*<br>*Vibrio cholerae*<br>*Clostridium perfringens* |
| | | α-2,3 (NeuAc from oligosaccharides) | *Salmonella typhimurium*<br>*Streptococcus pneumonia* |
| | | α-2/3,6 (NeuAc from complex) | *Clostridium perfringens* |
| β-Galactosidase | 3.2.1.23 | β-1/3,4,6 Gal linkages | Bovine testis<br>*Xanthamonas species*<br>*Streptococcus species*<br>*E. coli* |
| | | β-1/4,6 Gal linkages | Jack bean |
| | | β-1,4 Gal linkage | *Streptococcus pneumonia* |
| | | β-1,3-Gal linkage | *E. coli*<br>*Xanthomonas species* |
| | | β-1/3,6-Gal linkages | *Xanthomonas species*<br>*E. coli* |
| β-Hexosaminidase | 3.2.1.52<br>3.2.1.30 | β-1/2,3,4,6 hexosamines | *Streptococcus plicatus*<br>*Streptococcus pneumonia*<br>*Bacteroides*<br>Jack bean |
| α-Fucosidase | 3.2.1.51<br>3.2.1.111 | α-1-3,4-Fuc (usually de-glycosylate Lewis structure) | *Xanthomonas*<br>Almond meal |
| | | α-1/2,3,4,6-Fuc (usually has broad specificity) | Bovine kidney<br>*C. meningosepticum* |
| | | α-1,6-Fuc | *E. coli* |
| | | α-1,2-Fuc | *Xanthomonas* |
| α-Mannosidase | 3.2.1.24 | α-1/2,3,6-Man | Jack bean |
| | | α-1/2,3-Man | *Xanthomonas manihotis* |
| | | α-1,6-Man (typically a core mannosidase) | *Xanthomonas species* |
| | | α-1,2-Man | *Aspergillus saitoi* |
| β-Mannosidase | 3.2.1.25 | α-1,4-Man | *Helix pomatia* |

*"EC #" refers to Enzyme Commission registration number

According to the present disclosure, glycans that have been released from a glycoprotein and/or a cell surface can be digested with any exoglycosidase. In certain embodiments, glycans are digested by subjecting a population of glycans to a plurality of exoglycosidases. For example, a population of glycans may be subjected to 2, 3, 4, 5, 6, 7, 8, 9, 10, or more exoglycosidases. In some embodiments, multiple exoglycosidases are administered simultaneously. In some embodiments, multiple exoglycosidases are administered sequenmethods for analyzing glycans are known in the art. For example, see Anumula, Anal. Biochem, 350(1):1-23, 2006; Klein et al. Anal. Biochem., 179:162-66, 1989; and Townsend, R. R., *Carbohydrate Analysis High Performance Liquid Chromatography and Capillary Electrophoresis*, ed. Z. El Rassi, pp. 181-209, 1995, Yuan et al., J. Chromatography A (2005) 1067:145-152, each of which in incorporated herein by reference in its entirety.

In certain embodiments, cell-surface glycans are liberated from the cell prior to analyzing their structure (e.g., via treatment with proteases and/or glycosidases such as described above). The glycosylation pattern of liberated cell-surface glycoproteins can be analyzed by one or more of a variety of methods. As non-limiting examples, glycosylation patterns of liberated cell-surface glycans can be characterized by methods such as NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other methods that can be used to characterize liberated cell-surface glycans.

In certain embodiments, cell-surface glycans are not liberated from the cell prior to analyzing their structure. The pattern of cell-surface glycans that are attached to the cell surface can be analyzed by one or more of a variety of methods.

As non-limiting examples, cell-surface glycans can be characterized by methods such as antibody binding, lectin binding, and combinations thereof. The binding of an antibody, lectin or other agent that recognizes one or more specific glycan structures, can be monitored by any of a variety of techniques including, for example, immunofluorescence, chemiluminescence, ELISA assays, flow cytometry, etc. Those of ordinary skill in the art will be aware of other methods that can be used to characterize glycosylation patterns of cell-surface glycans on the surface of cells.

In certain embodiments, cell-surface glycans are analyzed by being released from cells, purified, and then analyzed. For example, in some embodiments, such glycans are characterized by methods such as chromatographic methods, mass spectroscopic methods, electrophoretic methods, nuclear magnetic resonance (NMR) methods, and combinations thereof. For example, in some embodiments, glycans are characterized by one or more of NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof.

In some embodiments, N-glycan structure and composition can be analyzed by chromatographic methods, including but not limited to, liquid chromatography (LC), high performance liquid chromatography (HPLC), ultra performance liquid chromatography (HPLC), thin layer chromatography (TLC), amide column chromatography, and combinations thereof.

In some embodiments, N-glycan structure and composition can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, N-glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, N-glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

Those of ordinary skill in the art will be aware of other methods that can be used to characterize glycosylation patterns of liberated cell surface glycoproteins.

In certain embodiments, cell-surface glycoprotein and/or glycan structures are labeled prior to characterization. As is known to those of ordinary skill in the art, such labeling may increase signal and/or reduce background noise during characterization. Any of a variety of labels can be used in accordance with the present disclosure, including but not limited to, fluorescent labels, radiolabels and/or chemiluminescent labels. In certain embodiments, glycan structures are labeled with fluorescent 2-aminobenzamide ("2-AB"). Those of ordinary skill in the art will be aware of other suitable labels that can be used in accordance with the present disclosure.

Applications

It will be appreciated that the techniques described herein can be utilized in any of a variety of applications. In general, these techniques are useful in any application that involves the structural characterization of glycans, and is particularly useful where it is desirable to characterize glycans associated with a target glycoconjugate (e.g., glycoprotein) but isolation of the target glycoconjugate is time or labor intensive or poses other challenges (e.g., associated with instability of the glycoconjugate, etc.)

Methods of the present disclosure can be applied to glycans obtained from a wide variety of sources including, but not limited to, therapeutic formulations and biological samples (e.g., containing cells). Such a biological sample may undergo one or more analysis and/or purification steps prior to or after being analyzed according to the present disclosure. To give but a few examples, in some embodiments, a biological sample is treated with one or more proteases and/or glycosidases (e.g., so that glycans are released); in some embodiments, cell surface glycans in a biological sample are labeled with one or more detectable markers or other agents that may facilitate analysis by, for example, mass spectrometry or NMR. Any of a variety of separation and/or isolation steps may be applied to a biological sample in accordance with the present disclosure.

The present disclosure can be utilized to analyze cell surface glycans in any of a variety of states including, for instance, free glycans, glycoconjugates (e.g., glycopeptides, glycolipids, proteoglycans, etc.), or cells or cell components, etc.

Methods of the present disclosure may be used in one or more stages of process development for the production of a therapeutic or other commercially relevant glycoprotein of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

The present disclosure can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The present disclosure can also be utilized to assess glycosylation characteristics of cells or cell lines that are being considered for production of a particular desired glycoprotein (for example, even before the cells or cell lines have been engineered to produce the glycoprotein, or to produce the glycoprotein at a commercially relevant level).

In some embodiments of the disclosure, a desired glycosylation pattern for a particular target glycoprotein is known, and the technology described herein allows monitoring of culture samples to assess progress of the production along a route known to produce the desired glycosylation pattern. For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

In some embodiments, methods in accordance with the disclosure may be used to monitor the cell surface glycosylation pattern during culture of cells that produce a glycoprotein. For example, production of a glycoprotein (e.g., commercial production) may involve steps of (1) culturing cells that produce the glycoprotein, (2) obtaining samples at regular or irregular intervals throughout the process of culturing the cells, and (3) analyzing the cell surface glycosylation pattern on obtained samples. In some embodiments, such methods may further comprise a step of comparing the cell surface glycosylation patterns of different samples to one another and/or to glycosylation patterns of one or more non-cell-surface glycoproteins produced by the relevant cell(s). In some embodiments, such methods may further comprise a step of comparing the cell surface glycosylation patterns for one or more obtained samples to the glycosylation pattern of a reference sample.

In some embodiments of the present disclosure, a desired glycosylation pattern (e.g, a cell surface glycosylation pattern and/or a glycosylation patterns observed with a produced non-cell-surface glycoprotein) will be more extensive. For example, in some embodiments, a desired glycosylation pattern shows high (e.g., greater than about 60%, about 65%, about 70%, about 75%, about 80%, about 85%, about 90%, about 95%, about 98%, about 99%, or more) occupancy of glycosylation sites; in some embodiments, a desired glycosylation pattern shows, a high degree of branching (e.g., greater than about 60%, about 65%, about 70%, about 75%, about 80%, about 85%, about 90%, about 95%, about 98%, about 99% or more have tri or tetra-antennary structures).

In some embodiments of the present disclosure, a desired glycosylation pattern will be less extensive. For example, in some embodiments, a desired cell surface glycosylation pattern shows low (e.g., less than about 50%, about 45%, about 40%, about 35%, about 30%, about 25%, about 20%, about 15%, about 15%, about 5%, about 1%, or less) occupancy of glycosylation sites; and/or a low degree of branching (e.g., less than about 20%, about 15%, about 10%, about 5%, about 1% or less have tri or tetra-antennary structures).

In some embodiments, a desired glycosylation pattern will be more extensive in some aspects and less extensive in others. For example, it may be desirable to employ a cell line that tends to produce glycoproteins with long, unbranched oligosaccharide chains. Alternatively, it may be desirable employ a cell line that tends to produce glycoproteins with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, about 15%, about 10%, about 5%, about 1%, or less) of high mannose or hybrid structures, high levels (e.g., greater than about 60%, about 65%, about 70%, about 75%, about 80%, about 85%, about 90%, about 95%, about 98%, about 99%, or more) of high mannose structures, high levels (e.g., greater than about 60%, about 65%, about 70%, about 75%, about 80%, about 85%, about 90%, about 95%, about 98%, about 99%, or more; for example at least one per glycoprotein) phosphorylated high mannose, or low levels (e.g., less than about 20%, about 15%, about 10%, about 5%, about 1%, or less) of phosphorylated high mannose.

In some embodiments, a desired glycosylation pattern will include at least about one sialic acid. In some embodiments, a desired glycosylation pattern will include a high level (e.g., greater than about 60%, about 65%, about 70%, about 75%, about 80%, about 85%, about 90%, about 95%, about 98%, about 99%, or more) of termini that are sialylated. In some embodiments, a desired glycosylation pattern that includes sialyation will show at least about 85%, about 90%, about 95%, about 98%, about 99%, or more N-acetylneuraminic acid and/or less than about 20%, about 15%, about 10%, about 5%, about 1%, or less N-glycolylneuraminic acid.

In some embodiments, a desired glycosylation pattern shows specificity of branch elongation (e.g., greater than about 60%, about 65%, about 70%, about 75%, about 80%, about 85%, about 90%, about 95%, about 98%, about 99%, or more of extension is on $\alpha 1,6$ mannose branches; or greater than about 60%, about 65%, about 70%, about 75%, about 80%, about 85%, about 90%, about 95%, about 98%, about 99%, or more of extension is on $\alpha 1,3$ mannose branches).

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of core fucosylation.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sulfated glycan In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a phosphorylated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sialic acid linked to an N-acetylglucosamine.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of an acetylated glycan.

Whether or not monitoring production of a particular target protein for quality control purposes, the present disclosure may be utilized, for example, to monitor cell surface glycosylation at particular stages of development, or under particular growth conditions.

In some particular embodiments of the present disclosure methods described herein can be used to characterize and/or control or compare the quality of therapeutic products. To give but one example, the present methodologies can be used to assess cell surface glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of cell surface glycosylation in production systems for therapeutic proteins.

Whether or not monitoring production of a particular target protein for quality control purposes, the present disclosure may be utilized, for example, to monitor glycosylation at particular stages of development, or under particular growth conditions.

In some embodiments, methods described herein can be used to characterize and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for instance, erythropoietin, blood-clotting factors, etc.), interferons, colony stimulating factors, antibodies, enzymes, and hormones, particularly those that are expressed on the cell surface.

In some embodiments, the disclosure provides methods in which cell surface glycans from different sources or samples are compared with one another. In some such examples, multiple samples from the same source are obtained over time, so that changes in glycosylation patterns (and particularly in cell surface glycosylation patterns) are monitored. In some embodiments, glycan-containing samples are removed at regular intervals. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments, one of the samples is a historical sample or a record of a historical sample. In some embodiments, one of the samples is a reference sample.

As described herein, in certain embodiments, methods of the present disclosure are useful in determining one or more characteristics of the glycosylation pattern of a glycoprotein produced by a cell. In certain embodiments, such methods may comprise steps of: determining a difference in glycosylation pattern between a first surface glycosylation pattern present under a first set of conditions on the surface of a cell that produces a glycoprotein of interest and a second surface glycosylation pattern present under a second set of conditions on the surface of the cell, and based on the determined difference, establishing one or more characteristics of the glycosylation pattern of the glycoprotein of interest produced by the cell. For example, glycosylation pattern of a glycoprotein of interest over time can be determined by determining glycosylation patterns present on the surface of the cells at different time points of a cell culture.

Additionally or alternatively, changes in the glycosylation pattern of a glycoprotein of interest grown under one or more different growth parameters can be tested to determine one or more desirable growth parameters, or combinations of parameters, for glycoprotein production. In certain embodiments, differences in glycosylation patterns are determined by observing and/or measuring a glycosylation pattern characteristic such as, without limitation, glycosylation site occupancy, identity of linked glycans, relative amounts of linked glycans, complete or partial composition of linked glycans, and/or relative amounts of linked glycans. Methods of the present disclosure encompass observing and/or measuring other glycosylation pattern characteristics known to those of ordinary skill in the art.

In some particular embodiments, methods described herein can be used to characterize and/or control or compare the quality of therapeutic products without requiring isolation of the products themselves. To give but one example, according to the present disclosure methodologies described herein can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of glycosylation in production systems for therapeutic proteins.

In some embodiments, methods provided herein are used to monitor the extent and/or type of glycosylation occurring in different samples (e.g., in different cell cultures).

In some embodiments, glycans from different cell culture samples prepared under conditions that differ in one or more selected parameters (e.g., cell type, culture type [e.g., continuous feed vs batch feed, etc.], culture conditions [e.g., type of media, presence or concentration of particular component of particular medium(a), osmolarity, pH, temperature, timing or degree of shift in one or more components such as osmolarity, pH, temperature, etc.], culture time, isolation steps, etc.) but are otherwise identical, are compared, so that effects of the selected parameter(s) on N-glycosylation patterns are determined. In certain embodiments, glycans from different cell culture samples prepared under conditions that differ in a single selected parameter are compared so that effect of the single selected parameter on glycosylation patterns is determined. Among other applications, therefore, the present techniques may facilitate determination of the effects of particular parameters on glycosylation patterns in cells.

In some embodiments, cell surface glycans from different batches of cells that produce a glycoprotein of interest (e.g., a therapeutic glycoprotein), whether prepared by the same method or by different methods, and whether prepared simultaneously or separately, are compared. In such embodiments, the present disclosure facilitates quality control of glycoprotein preparation (i.e., of preparation of a target glycoprotein preparation). Alternatively or additionally, some such embodiments facilitate monitoring of progress of a particular culture producing a glycoprotein of interest (e.g., when samples are removed from the culture at different time points and are analyzed and compared to one another). In any of these embodiments, features of the glycan analysis can be recorded, for example in a quality control record. As indicated above, in some embodiments, a comparison is with a historical record of a prior or standard batch of glycoprotein, and/or with a reference sample.

In certain embodiments, the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

According to the present disclosure, techniques described herein can be used to detect desirable or undesirable glycans, for example to detect or quantify the presence of one or more contaminants in a product, or to detect or quantify the presence of one or more active or desired species.

In various embodiments the methods can be used to assess glycosylation of one or more biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time. For example, in some embodiments of the disclosure, the target glycoconjugate is a biomarker.

In certain embodiments, methods described herein facilitate detection of glycans (e.g., cell surface glycans) that are present at very low levels in a source (e.g., a biological sample). In such embodiments, it is possible to detect and/or optionally quantify the levels of cell surface glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans. In some embodiments, it is possible to detect and/or optionally quantify the levels of glycans comprising between 0.1% and 5%, e.g., between 0.1% and 2%, e.g., between 0.1% and 1% of a cell surface glycan preparation. In certain embodiments, it is possible to detect and/or optionally quantify the levels of glycans at between about 0.1 fmol to about 1 mmol.

In some embodiments, techniques described herein may be combined with one or more other technologies for the detection, analysis, and or isolation of glycans or glycoconjugates.

Kits

Reagents useful for the practice of one or more methods of the present disclosure may desirably be provided together, assembled in a kit. In certain embodiments, kits of the present disclosure include one or more reagents useful for liberating glycoproteins from the cell surface (e.g., one or more proteases, glycosidases, and/or other agents) and/or supplementary components such as buffers, co-factors, etc. In certain embodiments, kits of the present disclosure include one or more reagents useful for purifying and/or analyzing the liberated cell-surface glycoprotein from the cells from which they have been liberated.

In certain embodiments, kits of the present disclosure include one or more reagents useful for cleaving glycan structures from a glycoprotein or glycopeptide (e.g., enzymes such as PNGase F, PNGase A, O-glycanase and/or Endo-H). In certain embodiments, kits of the present disclosure include one or more reagents useful for purifying the cleaved glycan structures from the protein component of glycoproteins or glycopeptides (e.g., one or more glycosidases).

In certain embodiments, kits of the present disclosure include one or more reagents for labeling glycan structures. For example, kits of the present disclosure may include fluorescent labels, radiolabels and/or chemiluminescent labels. In certain embodiments, kits of the present disclosure include fluorescent 2-aminobenzamide ("2-AB").

In certain embodiments, kits of the present disclosure include one or more reagents for culturing cells (e.g., cell culture media, buffers, media components, etc.) and/or purifying cells after the cells have been cultured.

The foregoing description is to be understood as being representative only and is not intended to be limiting. Alternative methods and materials for implementing the disclosure and additional applications to which the present disclosure can be applied will be apparent to one of skill in the art, and are intended to be included within the accompanying claims.

EXEMPLIFICATION

Example 1

Detection of Cell-surface glycans Released by Exoglycosidase Treatment Reveals Parallel Changes in Cell Surface and Non-Cell Surface Glycosylation CHO cells that produced a cell-surface glycoprotein of interest (in this case, a non-cell-surface antibody) were cultured under standard conditions in two different media: a first medium containing a first amount of glucosamine and a second medium containing a second amount of glucosamine, wherein the second amount of glucosamine was higher than the first amount of glucosamine.

After a given period of growth in culture, cells and culture supernatant from the same culture flask were harvested. Cells were pelleted and washed with PBS to remove media components and culture supernatant was clarified prior to isolation of product antibody.

For product isolation, the culture supernatant was incubated with protein A sepharose beads overnight. Beads were then pelleted and washed with PBS. Product was eluted by low pH 0.1 M glycine solution.

One aliquot of the washed cells was treated with protease to release cell surface glycopeptides. Intact cells were separated from released cell surface glycopeptides by centrifugation Glycans were enzymatically released from the isolated product antibody or from released cell surface glycopeptides with PNGase F. The isolated glycans were fluorescently labeled and were treated with exoglycosidase (sialidase, galactosidase, and hexosaminidase) to collapse N-linked glycans down to the core M3N2; the glycans that were released by this treatment were analyzed by LC and/or MS, so that relative amounts of fucosylated and non-fucosylated glycans were determined.

FIG. 1 shows the percentage of nonfucosylated glycans observed for the non-cell-surface glycoprotein (antibody product) in the first (control) and second (elevated glucosamine) media; FIGS. 3A-B shows the same percentage observed for cell-surface glycans in the same media. FIG. 2 shows representative LC spectra for cell-surface glycans, as was included in the summarized data of FIGS. 3A-B.

As is evident in FIGS. 1 and 3, a similar increase in non-fucosylated structures (i.e., loss of core alpha1-6 fucosylation) is observed for both the non-cell-surface and the cell-surface glycan populations. These data demonstrate both that methods utilized in accordance with the present disclosure allow ready detection, isolation, and or analysis of cell-surface glycans and further demonstrate that changes in non-cell-surface glycosylation patterns can be reflected in analogous changes in cell surface glycosylation patters, such that detection of cell-surface glycans can act as a proxy for detection of non-cell-surface glycans.

Example 2

Detection of Cell-surface Glycans on Intact Cells or on Released Cell Surface Glycans Reveals Parallel Changes in Cell Surface and Non-Cell Surface Glycosylation CHO cells that produced a cell-surface glycoprotein of interest (in this case, a non-cell-surface antibody) were cultured under standard conditions in two different media: a first medium containing a first amount of N-acetylmannosamine and a second medium containing a second amount of N-acetylmannosamine, wherein the second amount of N-acetylmannosamine was higher than the first amount of N-acetylmannosamine.

After a given period of growth in culture, cells and cell culture supernatant form the same culture flask were harvested. Cells were pelleted and washed with PBS to remove media components. Culture supernatant was clarified.

Non-cell-surface antibody product was isolated from the culture supernatant by incubation with protein A sepharose beads overnight. Beads were then pelleted and washed with PBS. Product was eluted by low pH 0.1 M glycine solution.

One aliquot of washed cells was lysed by exposure to hypotonic solution, and the resulting membranes were pelleted.

Sialic acids were released from the isolated antibody product and the membranes by acid treatment, and were isolated by ion exchange chromatography. The resultant sialic acids were subsequently DMB (1,2-diamino-4,5-methylenedioxy-benzene-2HCl)-labeled, and analyzed by HPLC.

Concurrently, a second aliquot of washed cells was subjected to lectin staining and analyzed by flow cytometry. Sialic acid levels were determined for both the cell surface and the non-cell-surface glycan samples under each culture condition.

FIG. 4 shows a representative LC analysis of sialic acid levels from the cell surface. FIGS. 5-7 show relative amounts of sialic acid in cell surface and non-cell-surface glycans under the different culture conditions. As can be seen, a similar increase in sialic acid levels is observed in both the non-cell-surface and the cell-surface glycan populations when cells are grown in elevated levels of N-acetylmannosamine.

These data demonstrate both that the methods described herein allow ready detection, isolation, and or analysis of cell-surface glycans and further demonstrate that changes in non-cell-surface glycosylation patterns can be reflected in analogous changes in cell surface glycosylation patters, such that detection of cell-surface glycans can act as a proxy for detection of non-cell-surface glycans. Importantly, the data demonstrate the ability to monitor glycosylation of a product of interest in real time, without requiring isolation of the product itself.

Example 3

Effect of Glucosamine Supplementation on Cell Surface and Product Sialylation

CHO cells producing a glycoprotein product were cultured in the presence or absence of glucosamine supplementation. After 5 days, the cells and product were harvested and analyzed for sialic acid content separately. Cell surface sialic acid content was determined by anion exchange chromatography as illustrated in FIG. 8. The percentage change in sialic acid relative to no glucosamine supplementation is shown in Table 2 below for both the cell surface and product. The data in Table 2 are indicated as the average (S.D.) of replicates.

TABLE 2

Percent Decrease in Sialylation

| Fermentation Condition | % Decrease in Sialylation | |
| --- | --- | --- |
| | Product | Cell Surface |
| Glucosamine | 16% (2.8) | 20% (4.6) |

These data demonstrate that decreases in cell surface sialylation associated with glucosamine supplementation correlate with decreases in product sialylation.

EQUIVALENTS

Those skilled in the art will recognize, or be able to ascertain using no more than routine experimentation, many equivalents to the specific embodiments of the disclosure, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of, the group members are present in, employed in, or otherwise relevant to a given product or process.

Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the disclosure, or aspects of the disclosure, is/are referred to as comprising particular elements, features, etc., certain embodiments of the disclosure or aspects of the disclosure consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any exoglycosidase, any glycosidic linkage, any reaction condition, any method of purification, any method of product analysis, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A method of determining one or more characteristics of the glycosylation pattern of a recombinant non-cell surface glycoprotein of interest produced by a cell, the method comprising:
    a) providing a cell that produces the recombinant non-cell surface glycoprotein of interest, which cell has at least one cell-surface glycan attached to the surface of the cell, so that the cell has a cell surface glycosylation pattern;
    b) liberating at least one cell surface glycan from the cell;
    c) determining at least one characteristic of the cell surface glycosylation pattern selected from the group consisting of degree of glycosylation site occupancy, identity of at least one linked glycan, relative amounts of linked glycans, complete or partial composition of linked glycans, and combinations thereof; and
    d) based on the at least one determined characteristic, establishing one or more characteristics of the glycosylation pattern of the recombinant non-cell surface glycoprotein of interest, wherein the determined characteristic correlates with the one or more characteristics of the glycosylation pattern of the non-cell surface glycoprotein of interest.

2. The method of claim 1, wherein the at least one characteristic of the glycosylation pattern comprises a change in glycosylation pattern of the recombinant non-cell surface glycoprotein of interest.

3. The method of claim 1, wherein the step of establishing one or more characteristics comprises establishing an extent of sialylation present in the glycosylation pattern of the recombinant non-cell surface glycoprotein of interest.

4. The method of clam 1, wherein the step of liberating comprises exposing the cell to a protease.

5. The method of claim 4, wherein the step of exposing comprises subjecting the cell to protease treatment such that at least one cell surface glycoprotein is liberated, wherein the protease treatment does not substantially rupture cell membranes.

6. The method of claim 1, wherein the step of liberating comprises:
    a) cleaving one or more protein-linked cell-surface glycans from cell surface glycoproteins; and
    b) characterizing the one or more cleaved protein-linked cell-surface glycans.

7. The method of claim 6, wherein the protein-linked cell-surface glycan is an N-linked glycan.

8. The method of claim 6, wherein the protein-linked cell-surface glycan is an O-linked glycan.

9. The method of claim 6, wherein the protein-linked cell-surface qlycans comprise at least one sialic acid residue.

10. The method of claim 1, further comprising a step of recording information about at least one of the glycosylation patterns in a fixed medium.

11. The method of claim 1, wherein the recombinant non-cell surface glycoprotein of interest is selected from the group consisting of human somatropin, coagulation factor VIIa, coagulation IX, interferon alphacon-1, insulin glargine, and insulin.

12. The method of claim 1, wherein the recombinant non-cell surface glycoprotein of interest is a recombinant antibody.

13. The method of claim 12, wherein the recombinant antibody is selected from the group consisting of etanercept, infliximab, adalimumab, basiliximab, daclizumab, omalizumab, gemtuzumab, alemtuzumab, rituximab, cetuximab, bevacizumab, palivizumab, and abciximab.

14. The method of claim 1, wherein the recombinant non-cell surface glycoprotein of interest is a therapeutic protein product.

15. The method of claim 1, wherein the recombinant non-cell surface glycoprotein of interest is a commercial glycoprotein that is produced industrially.

16. The method of claim 14, wherein the therapeutic protein product is or comprises a product selected from the group consisting of: a hematologic agent, an interferon, a colony stimulating factor, an antibody, an enzyme, and a hormone.

17. The method of claim 16, wherein the therapeutic protein product is or comprises an antibody.

18. The method of claim 14, wherein the therapeutic protein of interest is characterized in that it has undergone regulatory review in one or more countries.

19. The method of claim 14, wherein the at least one characteristic of the glycosylation pattern of the therapeutic protein of interest is compared to a reference sample that is a pharmaceutical product which has an established glycosylation pattern.

20. The method of claim 19, wherein the surface glycosylation pattern of the cell has at least a 75% correlation to the established glycosylation pattern of the reference sample.

21. The method of claim 1, wherein the step of determining the at least one characteristic of the cell surface glycosylation pattern includes a mass spectrometry technique.

22. The method of claim 1, wherein the glycosylation pattern includes one or more glycan structures selected from the group consisting of high mannose structures, hybrid structures, phosphorylated high mannose, sialylated termini, N-acetylneuraminic acid, N-glycolylneuraminic acid, extension on $\alpha 1,6$ mannose branches, extension on $\alpha 1,3$ mannose branches, core fucosylation, sulfated glycans, phosphorylated glycans, sialic acid linked to an N-acetylglucosamine, and acetylated glycans.

* * * * *

UNITED STATES PATENT AND TRADEMARK OFFICE
CERTIFICATE OF CORRECTION

PATENT NO. : 8,338,088 B2
APPLICATION NO. : 12/595902
DATED : December 25, 2012
INVENTOR(S) : Brian E. Collins et al.

It is certified that error appears in the above-identified patent and that said Letters Patent is hereby corrected as shown below:

In claim 9, line 28, delete "qlycans" and insert --glycans-- therefor.

Signed and Sealed this
Twenty-sixth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,338,088 B2  
APPLICATION NO. : 12/595902  
DATED : December 25, 2012  
INVENTOR(S) : Brian E. Collins et al.

It is certified that error appears in the above-identified patent and that said Letters Patent is hereby corrected as shown below:

Column 32, line 28 (Claim 9, line 2) delete "qlycans" and insert --glycans-- therefor.

This certificate supersedes the Certificate of Correction issued March 26, 2013.

Signed and Sealed this  
Twenty-third Day of April, 2013

Teresa Stanek Rea  
*Acting Director of the United States Patent and Trademark Office*